US012636282B1

(12) United States Patent
Feng

(10) Patent No.: US 12,636,282 B1
(45) Date of Patent: \*May 26, 2026

(54) THERAPEUTIC METHOD AGAINST VIRAL INFECTION

(71) Applicant: Helen Feng, Palo Alto, CA (US)

(72) Inventor: Helen Feng, Palo Alto, CA (US)

( * ) Notice: Subject to any disclaimer, the term of this patent is extended or adjusted under 35 U.S.C. 154(b) by 587 days.

This patent is subject to a terminal disclaimer.

(21) Appl. No.: 18/130,406

(22) Filed: Apr. 3, 2023

Related U.S. Application Data

(63) Continuation of application No. 17/210,385, filed on Mar. 23, 2021, now Pat. No. 11,628,165, which is a continuation of application No. 17/074,547, filed on Oct. 19, 2020, now abandoned.

(60) Provisional application No. 62/994,765, filed on Mar. 25, 2020.

(51) Int. Cl.
| | |
|---|---|
| *A61K 31/198* | (2006.01) |
| *A61K 31/4706* | (2006.01) |
| *A61K 31/593* | (2006.01) |
| *A61K 38/17* | (2006.01) |
| *A61P 31/14* | (2006.01) |

(52) U.S. Cl.
CPC ........ *A61K 31/4706* (2013.01); *A61K 31/198* (2013.01); *A61K 31/593* (2013.01); *A61K 38/177* (2013.01); *A61P 31/14* (2018.01)

(58) Field of Classification Search
CPC .............................. A61K 31/198; A61P 31/14
See application file for complete search history.

(56) References Cited

U.S. PATENT DOCUMENTS 11,628,165 B1 * 4/2023 Feng .................... A61K 31/198
514/313

OTHER PUBLICATIONS

De Flora et al., "Rationale for the use of N-acetylcysteine in both prevention and adjuvant therapy of COVID-19," FASEB J. Oct. 2020;34(10):13185-93 (electronic publication Aug. 11, 2020). (Year: 2020).*
Nasi et al., "Reactive oxygen species as an initiator of toxic innate immune responses in retort to SARS-CoV-2 in an ageing population, consider N-acetylcysteine as early therapeutic intervention," Toxicol. Rep. Jun. 2020;7:768-71 (available online Jun. 18, 2020). (Year: 2020).*
Shi et al., "N-Acetylcysteine to Combat COVID-19: An Evidence Review," Ther. Clin. Risk Manag. Nov. 2020;16:1047-55 (published Nov. 2, 2020). (Year: 2020).*
Baidya, D. K., et al (2011). Pregabalin in acute and chronic pain. Journal of anaesthesiology, clinical pharmacology, 27(3), 307-314. https://doi.org/10.4103/0970-9185.83672.

"Rossi R, Talarico M, Coppi F, Boriani G. Protective role of statins in COVID 19 patients: importance of pharmacokinetic characteristics rather than intensity of action. Intern Emerg Med. 2020;15(8):1573-1576. doi:10.1007/sl 1739-020-02504-y."
Jakhmola et al. (Front. Physiol., Aug. 4, 2020, https://doi.org/10.3389/ fphys.2020.00984).
Mehmel, M et al. ( Nicotinamide Riboside—The Current State of Research and Therapeutic Uses. Nutrients 2020, 12, 1616. https:// doi.org/10.3390/nul206l 616).
Shi Z, Puyo CA. N-Acetylcysteine to Combat COVID-19: An Evidence Review. Ther Clin Risk Manag. 2020;16:1047-1055. Published Nov. 2, 2020. doi:10.2147/TCRM.S273700.
Nurshad Ali (Journal of Infection and Public Healthvol. 13, Issue 10, Oct. 2020, pp. 1373-1380 https://doi.org/10.1016/j.jiph. Jun. 21, 2020,Role of vitamin Din preventing ofCOVID-19 infec-tion, progression and severity ).
Heer et al. (Journal of Biological Chemistry, Published in issue: Dec. 25, 2020, vol. 295, Issue 52, p. 17889-18650).
Zoltan Szabo et al. (Front.Physiol. Jun. 19, 20201 https://doi.org/ 10.3389/fphys.2020 .00752,).
Veazie S, Peterson K, Ansari Y, et al. Fludrocortisone for orthostatic hypotension. Cochrane Database Syst Rev.2017;2017(12): CD012868. Published Dec. 4, 2017. doi:10.1002/14651858.CD012868.
ChromeDex Published on Oct. 6, 2020) View source version on businesswire. com: https://www.businesswire.com/news/home/ 20201006005386/en/.
Perez-Arredondo A, et al. (Baclofen in the Therapeutic of Sequele of Traumatic Brain Injury: Spasticity. Clin Neuropharmacol. 2016; 39(6):311-319. doi:10.1097/WNF.0000000000000179).
Patel et al., "Initial Public Health Response and Interim Clinical Guidance for the 2019 Novel Coronavirus Outbreak," Morb. Mortal. Wkly. Rep. (CDC) Feb. 2020;69:140-146. (Year: 2020).
Grandjean et al., "Efficacy of oral long-term N-acetylcysteine in chronic bronchopulmonary disease: a meta-analysis of published double-blind, placebo-controlled clinical trials," Clin. Ther. Feb. 2000;22(2):209-21. PMID: 10743980. (Year: 2000).
Tabas, Anti-inflammatory therapy in chronic disease: challenges and opportunities; Science; 339(6116): 166-72; Jan. 11, 2013.
Nathan, Nonresolving inflammation, Cell; 140(6): 871-82; Mar. 19, 2010.
Wu W., et al., Cigarette smoke extract suppresses the RIG-I-initiated innate immune response to influenza virus in the human lung, Am J Physiolo, Lung Cell Mo! Physiol; 300(6): L821-L830; Jun. 1, 2011.
Meltzer D., et al., Association of Vitamin D Status and Other Clinical Characteristics With COVID-19 Test Results, JAMA Network Open. 2020; 3(9): e2019722; Sep. 3, 2020.

(Continued)

*Primary Examiner* — Theodore R. Howell
(74) *Attorney, Agent, or Firm* — ROARK IP

(57) ABSTRACT

Coronavirus disease of 2019 (COVID-19) is an acute viral infection that can trigger complicated immune system responses depending on the host. This disclosure discloses immunotherapy methods combining immunomodulators and antivirals to prevent and to reduce the severity of a COVID-19 infection. Successful treatment of COVID-19 requires prevention, early recognition and detection, the ruling out of co-infections, serial laboratory monitoring, and clinical monitoring for worsening and timely treatments during the acute phase and post-viral syndrome. Using this disclosure as preventive, management and therapeutic options for COVID-19, infected patients can be more resilient to viral challenges, recovering faster with less organ damages and adverse residual effects.

15 Claims, 3 Drawing Sheets

(56) References Cited

OTHER PUBLICATIONS

Lai K.Y., et al., The W-Shaped Mortality-Age Distribution of Novel HINI Influenza Virus Helps Reconstruct the Second Wave of Pandemic 1918 Spanish Flu, J Pulmonary & Respiratory Medicine; 5(2): 1000245; 2015.

Sadowska A.M., N-Acetylcysteine mucolysis in the management of chronic obstructive pulmonary disease, Therapeutic Advances in Respiratory Disease; 6(3): 127-35; Jun. 2012.

Ortolani O., et al., Glutathione and N-acetylcysteine in the prevention of free-radical damage in the initial phase of septic shock, Recenti Prag Med; 93(2): 125-9; Feb. 2002.

Kupczyk M., Mucolytics in acute and chronic respiratory tract disorders. II. Uses for treatment and antioxidant properties, Pol Merkur Lekarski; 12(69): 248-52; Mar. 2002.

Mata M., et al., N-acetyl-L-cysteine (NAC) inhibit mucin synthesis and pro-inflammatory mediators in alveolar type II epithelial cells infected with influenza virus A and B and with respiratory syncytia virus (RSV), Biochem Pharmacol; 82(5): 548-55; Sep. 1, 2011.

De Flora S., Attenuation of influenza-like symptomatology and improvement of cell-mediated immunity with long-term N-acetylcysteine treatment, European Respiratory Journal; 10(7): 1535-41; Jul. 1997.

Lai ZW., et al., N-acetylcysteine reduces disease activity by blocking mammalian target of rapamycin in T cells from systemic lupus erythematosus patients: a randomized, double-blind, placebo-controlled trial, Arthritis Rheum; 64(9): 2937-46; Sep. 2012.

Cappellini M., Glucose-6-phosphate dehydrogenase deficiency, Lancet; 371(9606): 64-74; Jan. 5, 2008.

Uyoga S., Glucose-6-phosphate dehydrogenase deficiency and the risk of malaria and other diseases in children in Kenya: a case-control and a cohort study, The Lancet Hematology; 2(10); E437-E444; Oct. 1, 2015.

Petri M., et al., Hydroxychloroquine Blood Levels Predict Hydroxychloroquine Retinopathy, Arthritis Rheum;72(3): 448-453.; epub Jan. 7, 2020.

Melles R. & Marmor M., The Risk of Toxic Retinopathy in Patients on Long-term Hydroxychloroquine Therapy, JAMA Ophthalmol. 2014; 132(12): 1453-1460; Dec. 2014.

Zhou F., et al., Clinical course and risk factors for mortality of adult inpatients with COVID-19 in Wuhan, China: a retrospective cohort study, The Lancet; 395(10229): 1054-1062; Mar. 28, 2020.

Sakabe M., Sick sinus syndrome induced by interferon and ribavirin therapy in a patient with chronic hepatitis C, J Cardiology Case; 8(6):173-175; Dec. 1, 2013.

Xie J., et. al., Association Between Hypoxemia and Mortality in Patients With COVID-19, Mayo Clin Proc; 95(6):1138-1147; Jun. 1, 2020.

Linder D., et al., Association of Cardiac Infection With SARS-CoV-2 in Confirmed COVID-19 Autopsy Cases, JAMA Cardiol. 2020; 5(11): 1281-1285; epub Jul. 27, 2020.

Horby P., et al., Dexamethasone in Hospitalized Patients with Covid-19-Preliminary Report, New England Journal of Medicine; epub Jul. 17, 2020.

Yao T.C., et al., Association Between Oral Corticosteroid Bursts and Severe Adverse Events : A Nationwide Population-Based Cohort Study, Annals of Internal Medicine; 173(5):325-330; epub Jul. 7, 2020.

Waljee A.K., et al., Short term use of oral corticosteroids and related harms among adults in the United States: population based cohort study, BMJ 2017; 357:jl415, Apr. 12, 2017.

Puntmann V.O., et al., Outcomes of Cardiovascular Magnetic Resonance Imaging in Patients Recently Recovered From Coronavirus Disease 2019 (COVID-19), JAMA Cardiolology; epub Jul. 27, 2020.

Szekely Y., et al., Spectrum of Cardiac Manifestations in Covid-19—A Systematic Echocardiographic Study, Circulation; 142(4): 342-353; May 29, 2020.

Iwasaki A., Innate immunity to influenza virus infection, Nature Reviews Immunology; 14(5): 315-328; Apr. 25, 2014.

Mayo, "Coronavirus Disease 2019—COVID 2019" accessed from mayoclinic.org—May 16, 2022.

Luo et al., Journal of Medical Virology, 2020, 92(7); 814-818.

Balasubramanian et al., Indian Pediatrics, 2020, 57: 681-683.

Fischetti M et al., A Visual Guide to the SARS-CoV-2 Coronavirus, Scientific America; 323(1), Jul. 1, 2020.

Vasculera—diosmiplex 630, downloaded from https://dailymed.nlm.nih.gov/dailymed/fda/fdaDrugXsl.cfm?selid=563d3d34-a547-471e-aecd-f4a4a57cbf1d&type=display.

* cited by examiner

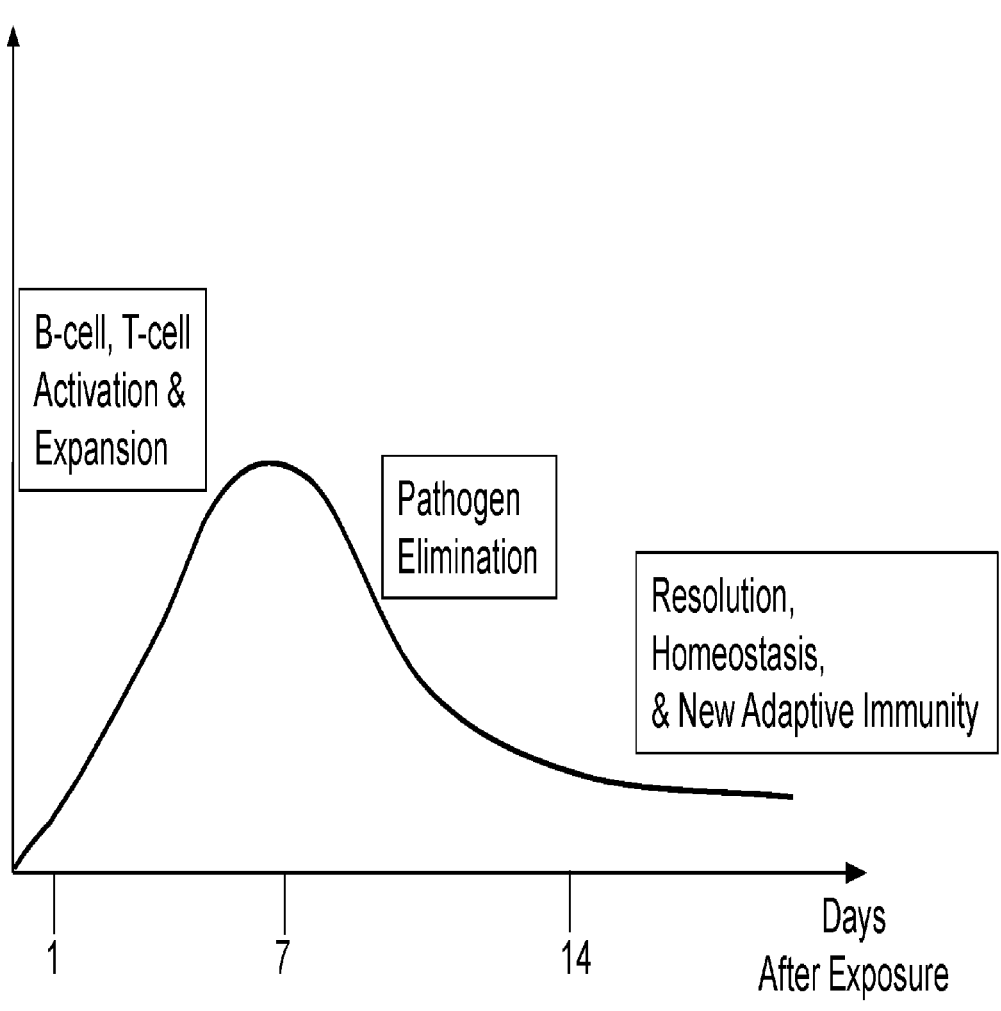
Figure 1A.  Normal Immune Response to Virus Infection

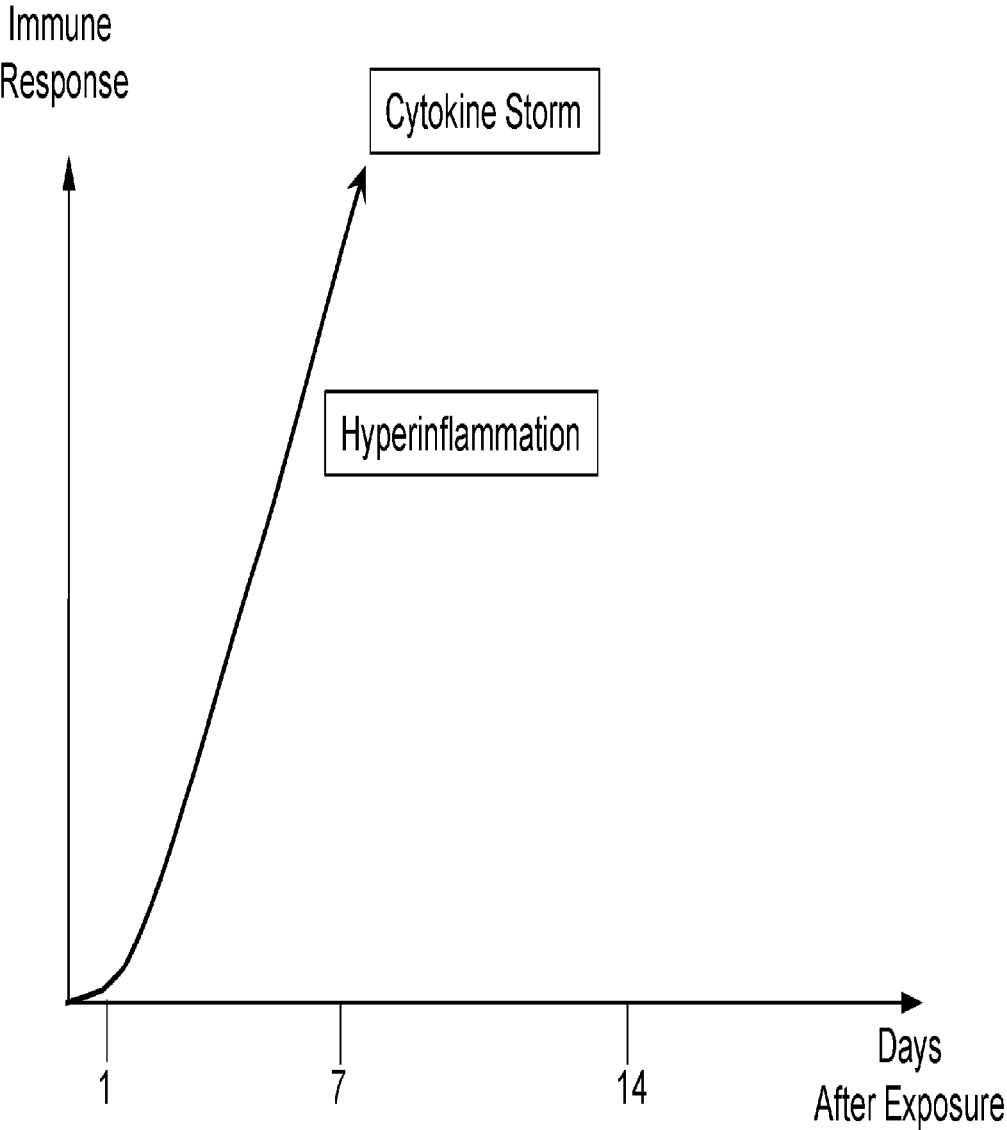
Figure 1B.  An Abnormal Immune Response to Virus Infection

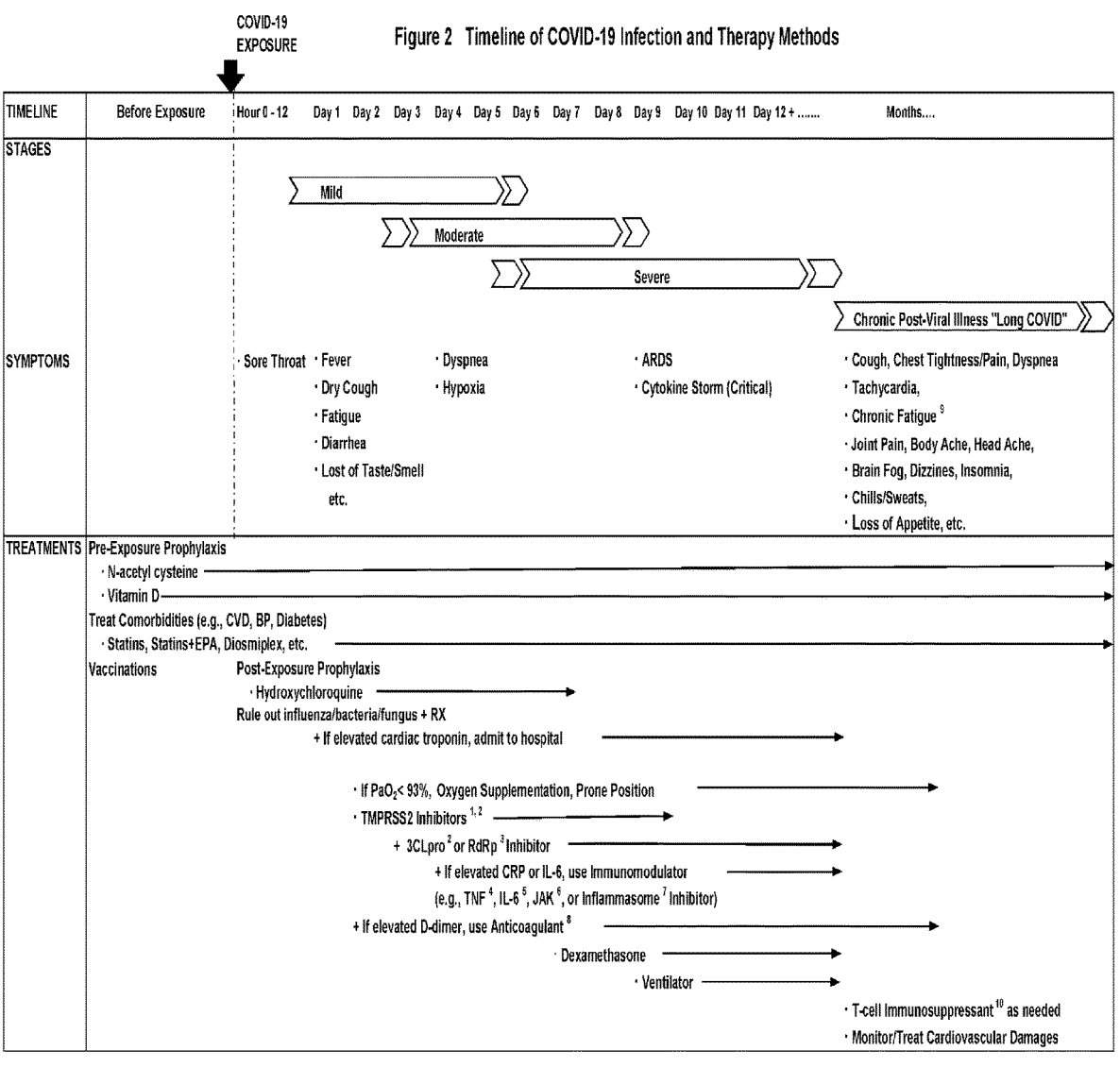

Figure 2   Timeline of COVID-19 Infection and Therapy Methods

Notes:

[1] TMPRSS2 Inhibitor: Nafamostat or Camostat to block SAR-COV2 S-protein initiated entry via ACE2 receptor

[2] 3CLpro inhibitor: Lopinavir-Ritonavir

[3] RdRp inhibitor: Favipiravir or Remdesivir

[4] TNF Inhibitor: Infliximab, Etanercept, Adalimumab, Certolizumab, or Golimumb

[5] IL-6 Inhibitor: Tocilizumab or Sarilumab

[6] JAK Inhibitor: Tofacitinib, Baricitinib, Upadacitinib. or Filgotinib

[7] Inflammasome Pathway Related Inhibitor: Dapansutrile (NLRP3), Colchicine (NLRP3) , Anakinra (IL-1β), or Canakinumab (IL-1)

[8] Anticoagulant: Heparin. Warfarin. Enoxaparin sodium, Acetylsalicylic Acid, Clopidogrel, or DOAC such as Apixaban, Dabigatran, Rivaroxaban, and Edoxaban

[9] Chronic Fatigue Treatment: Serotonin-Norepinephrine Reuptake Inhibitor (SNRI) or Anti-Epileptic. Tricyclic, Muscle Relaxant

[10] T-cell Immunosuppressant: Mycophenolate, Tacrolimus, Sirolimus.

THERAPEUTIC METHOD AGAINST VIRAL INFECTION

CROSS-REFERENCE TO RELATED APPLICATIONS

This application claims the benefit of U.S. patent application Ser. No. 17/210,385, filed on Mar. 23, 2021; which claims the benefit of U.S. Patent Provisional Application No. 62/994,765 filed Mar. 25, 2020 and U.S. patent application Ser. No. 17/074,547 filed Oct. 19, 2020. These applications are hereby incorporated herein in their entireties by reference.

FIELD OF THE DISCLOSURE

This disclosure relates to the field of virology. In particular, this disclosure relates to methods for boosting immune system against viral infections, treating viral infections, and post-viral syndrome, including coronavirus disease of 2019 (COVID-19).

BACKGROUND OF THE DISCLOSURE

Infectious diseases, whether or bacterial, viral, or other origin, present acute and chronic challenges to human health. Many common infections affect the respiratory tract. Respiratory tract diseases, particularly infectious respiratory diseases of viral and bacterial origin, are prevalent in patients of all ages, although often are more serious in the very old.

SUMMARY

Aspects of the disclosure include a method for pre-treating and treating a patient for infection by a coronavirus comprising: treating the patient with hydroxychloroquine (HCQ) 400 milligrams (mg) twice a day on a first day of exposure to the coronavirus and then decreasing to 200 mg twice a day for 5 to 10 days to inhibit the coronavirus and host cell angiotensin-converting enzyme 2 (ACE2) receptor binding, to interfere with the coronavirus and host cell fusion to decrease the efficiency of viral entry, replication and infection. Further aspects of the method include: pre-treating before exposure to prevent the coronavirus and post-infection treating the patient using N-acetyl cysteine (NAC) approximately 600 to 3000 milligrams (mg) daily to achieve at least one of the group consisting of: improve immunosurveillance in sensing the coronavirus pathogen, protect patient organs from failure caused by reactive oxygen species (ROS) of inflammation, enhance IFN-induced gene expression of antiviral proteins, and reduce the risk of cytokine storm by inhibiting mammalian target of rapamycin (mTOR). Further aspects of the method include: pre-treating with vitamin D3 approximately 2000 to 5000 international units (IU) daily to boost the patient's innate immune system. Further aspects of the method include: treating with at least one from the group consisting of: statin to reduce cardiovascular risks, statin plus eicosapentaenoic acid (EPA) at 2 grams twice daily to reduce cardiovascular risks, and Diosmiplex approximately 630 mg one to three times daily to improve circulation and to reduce inflammation for endothelial protection. Further aspects of the method include: treating a patient whose inflammation has further worsened to acute respiratory distress syndrome (ARDS) with dexamethasone.

Further aspects of the disclosure include: a method for pre-treating and treating a patient for a coronavirus infection comprising: if the coronavirus infection is progressing to a moderate stage, treating the patient with a transmembrane protease serine 2 (TMPRSS2) enzyme inhibitor to prevent the activation of S-protein on the coronavirus to gain entry to the patient's host cells thru angiotensin-converting enzyme 2 (ACE2) receptors, wherein the TMPRSS2 enzyme inhibitor is from at least one in the group: nafamostat and camostat. Further aspects of the method include: pretreating before exposure to prevent the coronavirus and post-infection treating the patient using N-acetyl cysteine (NAC) approximately 600 to 3000 milligrams (mg) daily to achieve at least one of the group consisting of: improve immunosurveillance in sensing the coronavirus pathogen, protect patient organs from failure caused by reactive oxygen species (ROS) of inflammation, enhance IFN-induced gene expression of antiviral proteins, and reduce the risk of cytokine storm by inhibiting mammalian target of rapamycin (mTOR). Further aspects of the method include: pretreating with vitamin D3 approximately 2000 to 5000 international units (IU) daily to boost the patient's innate immune system. Further aspects of the method include: pretreating before exposure to prevent the coronavirus and post-infection treating the patient using N-acetyl cysteine (NAC) approximately 600 to 3000 milligrams (mg) daily to achieve at least one of the group consisting of: improve immunosurveillance in sensing the coronavirus pathogen, protect patient organs from failure caused by reactive oxygen species (ROS) of inflammation, enhance IFN-induced gene expression of antiviral proteins, and reduce the risk of cytokine storm by inhibiting mammalian target of rapamycin (mTOR); and pretreating with vitamin D3 approximately 2000 to 5000 international units (IU) daily to boost the patient's innate immune system. Further aspects of the method include: treating with at least one from the group consisting of: statin to reduce cardiovascular risks, statin plus eicosapentaenoic acid (EPA) at 2 grams twice daily to reduce cardiovascular risks, and Diosmiplex approximately 630 mg one to three times daily to improve circulation and to reduce inflammation for endothelial protection. Further aspects of the method include: treating a patient whose inflammation has further worsened to acute respiratory distress syndrome (ARDS) with dexamethasone. Further aspects of the method include: a 3C-like protease protein (3CLpro) inhibitor or a RNA-dependent RNA polymerase (RdRp) inhibitor, if the coronavirus infection has progressed to a moderate stage with cough, dyspnea or hypoxia, or if chest x-ray or chest CT indicating evidence of pneumonia, lung inflammation or lung damage.

Further aspects of the disclosure include a method for pre-treating and treating a patient for a coronavirus infection comprising: if the coronavirus infection has progressed to a moderate stage with cough, dyspnea or hypoxia, or if a chest x-ray or chest computed tomography (CT) indicates evidence of pneumonia, lung inflammation or lung damage, treating the patient with at least one antiviral from a group consisting of: 3C-like protease protein (3CLpro) inhibitor and RNA-dependent RNA polymerase (RdRp) enzyme inhibitor. Further aspects of the method include: pretreating before exposure to prevent the coronavirus and post-infection treating the patient using N-acetyl cysteine (NAC) approximately 600 to 3000 milligrams (mg) daily to achieve at least one of the group consisting of: improve immunosurveillance in sensing the coronavirus pathogen, protect patient organs from failure caused by reactive oxygen species (ROS) of inflammation, enhance IFN-induced gene expression of antiviral proteins, and reduce the risk of cytokine storm by inhibiting mammalian target of rapamycin (mTOR). Further aspects of the method include: pretreating with vitamin D3 approximately 2000 to 5000 international units (IU) daily to boost the patient's innate immune system. Further aspects of the method include: pretreating before exposure to prevent the coronavirus and post-infection treating the patient using N-acetyl cysteine (NAC) approximately 600 to 3000 milligrams (mg) daily to achieve at least one of the group consisting of: improve immunosurveillance in sensing the coronavirus pathogen, protect patient organs from failure caused by reactive oxygen species (ROS) of inflammation, enhance IFN-induced gene expression of antiviral proteins, and reduce the risk of cytokine storm by inhibiting mammalian target of rapamycin (mTOR); and pretreating with vitamin D3 approximately 2000 to 5000 international units (IU) daily to boost the patient's innate immune system. Further aspects of the method include: treating with at least one of the group consisting of: statin to reduce cardiovascular risks, statin plus eicosapentaenoic acid (EPA) at 2 grams twice daily to reduce cardiovascular risks, and Diosmiplex approximately 630 mg one to three times daily to improve circulation and to reduce inflammation for endothelial protection. Further aspects of the method include: treating a patient whose inflammation has further worsened to acute respiratory distress syndrome (ARDS) with dexamethasone. Further aspects of the method include: wherein the 3CLpro inhibitor is lopinarvir-ritonavir for 200/50 mg 2 tablets used twice a day for 5 to 10 days. Further aspects of the method include: wherein the RdRp inhibitor is used for 5 to 10 days and is from at least one from the group consisting of: favipiravir and remdesivir.

Further aspects of the disclosure include: a method for treating a coronavirus infection in a patient comprising: for pre-infected patients: diagnose and treat to the target of co-morbidities including diabetes, hypertension, lung diseases, obesity; reduce cardiovascular risks with statins or statins plus eicosapentaenoic acid (EPA); boost immune system with N-acetyl cysteine (NAC), vitamin D3, a prebiotic and a probiotic; and take at least one of the group consisting of: a pneumonia vaccine and an influenza vaccination unless contraindicated; for exposed patients: continue with NAC; use Diosmiplex; use hydroxychloroquine; treat co-infections; test for COVID-19 antigens; test for influenza; perform blood tests complete blood count (CBC), comprehensive metabolic, C-reactive protein (CRP), interleukin 6 (IL-6), D-dimer, lactate dehydrogenase (LDH), high sensitivity cardiac troponin I; perform at least one of the following group: fever workup consist of blood culture, urine culture, chest x-ray, electrocardiogram (EKG); for COVID-19 infected outpatient treatment: steps of exposed patients above; continue with N-acetyl cysteine; use hydroxychloroquine or a 3C-like protease protein (3CLpro) inhibitor antiviral; use oxygen supplementation to keep oxygen saturation greater than approximately 93%; treat co-infections including bacterial, influenza, other viruses, and fungus; if moderate shortness of breath or O2 saturation in the low 90s despite oxygen supplementation use prone position; take an anticoagulation, if D-dimer is above normal; take biological immunomodulators, if C-reactive protein (CRP) is elevated indicating possible onset of cytokine storm; for hospitalization: steps of COVID-19 infected outpatient treatment above; conduct fever work-up; start convalescent plasma treatment; start nafamostat, if not available or if no improvement add remdesivir intravenous (IV) treatment; take a biologic immunomodulator if C-reactive protein (CRP) is elevated indicating possible onset of cytokine storm; take dexamethasone for acute respiratory distress syndrome (ARDS) or anticipating development to ARDS; and intubation or extracorporeal membrane oxygenation (ECMO) when critical.

A method for treating a patient for a coronavirus infection which is progressing to hyper-inflammation comprising: testing the patient's C-reactive protein (CRP) and if CRP is above approximately 30 milligram per liter (mg/L), or testing the patient's interleukin-6 (IL-6) and if IL-6 is above approximately 7 picograms per milliliter (pg/ml), then treating the patient with an immunomodulator from one of a group consisting of: tumor necrosis factor (TNF) inhibitor, IL-6 inhibitor, janus kinase (JAK) inhibitor, and inflammasome pathway related inhibitor. Further aspects of the method include: wherein the TNF inhibitor is from the group consisting of: infliximab, etanercept, adalimumab, certolizumab, and golimumab. Further aspects of the method include: wherein the IL-6 inhibitor is from the group consisting of: tocilizumab approximately 4 to 8 milligrams (mg) per kilogram body weight intravenously (IV), tocilizumab approximately 162 to 324 mg subcutaneously and sarilumab approximately 200 to 400 milligrams subcutaneously per day. Further aspects of the method include: wherein the JAK inhibitor is from the group consisting of: tofacitinib, baricitinib, upadacitinib, and filgotinib. Further aspects of the method include: wherein the inflammasome pathway related inhibitor is at least one from the group consisting of: a nucleotide-binding oligomerization domain-like receptor family pyrin domain containing 3 (NLRP3)-inflammasome inhibitor dapansutrile or colchicine, an interleukin-1 beta (IL-1 beta) inhibitor anakinra, and an interleukin-1 (IL-1) inhibitor canakinumab. Further aspects of the method include: pretreating before exposure to prevent the coronavirus and post-infection treating the patient using N-acetyl cysteine (NAC) approximately 600 to 3000 milligrams (mg) daily to achieve at least one of the group consisting of: improve immunosurveillance in sensing the coronavirus pathogen, to protect patient organs from failure caused by reactive oxygen species (ROS) of inflammation, to enhance IFN-induced gene expression of antiviral proteins, and to reduce the risk of cytokine storm by inhibiting mammalian target of rapamycin (mTOR). Further aspects of the method include: pretreating with vitamin D3 approximately 2000 to 5000 international units (IU) daily to boost the patient's innate immune system. Further aspects of the method include: treating with at least one from the group consisting of: statin to reduce cardiovascular risks, statin plus eicosapentaenoic acid (EPA) at 2 grams twice daily to reduce cardiovascular risks, and Diosmiplex approximately 630 mg one to three times daily to improve circulation and to reduce inflammation for endothelial protection. Further aspects of the method include: treating a patient whose inflammation has further worsened to acute respiratory distress syndrome (ARDS) with dexamethasone.

Further aspects of the disclosure include: a method for treating a coronavirus infection comprising: treating a coronavirus infected patient with a statin and eicosapentaenoic acid (EPA) at approximately 2 to 6 grams daily to reduce the patient's risks of heart attack, stroke, and cardiovascular damage during the coronavirus infection and subsequent post-acute residual damage or chronic damage. Further aspects of the method include: pretreating before exposure to prevent the coronavirus and post-infection treating the patient using N-acetyl cysteine (NAC) approximately 600 to 3000 milligrams (mg) daily to achieve at least one of the group consisting of: improve immunosurveillance in sensing the coronavirus pathogen, to protect patient organs from failure caused by reactive oxygen species (ROS) of inflammation, to enhance IFN-induced gene expression of antiviral proteins, and to reduce the risk of cytokine storm by inhibiting mammalian target of rapamycin (mTOR). Further aspects of the method include: pretreating with vitamin D3 approximately 2000 to 5000 international units (IU) daily to boost the patient's innate immune system. Further aspects of the method include: treating with at least one from the group consisting of: statin to reduce cardiovascular risks, statin plus eicosapentaenoic acid (EPA) at 2 grams twice daily to reduce cardiovascular risks, and Diosmiplex approximately 630 mg one to three times daily to improve circulation and to reduce inflammation for endothelial protection.

Further aspects of the disclosure include: a method for treating a post-acute coronavirus patient with residual inflammatory diseases with T-cell immunosuppressant, wherein the T-cell immunosuppressant is at least one from the group consisting of: mycophenolate, tacrolimus, and sirolimus.

Further aspects of the disclosure include a method for treating coronavirus infection comprising: if D-dimer is greater than the value of approximately 0.5 micrograms per milliliter (mcg/ml) then use one of the anticoagulants from the group consisting of: heparin, warfarin, enoxaparin sodium, acetylsalicylic acid, clopidogrel, apixaban, dabigatran, rivaroxaban, and edoxaban. Further aspects of the method include: wherein if D-dimer is elevated higher than 0.5 mcg/ml then obtain computed tomography (CT) angiogram to rule out pulmonary embolism (PE) and a lower extremity ultrasound to rule out deep venous thrombosis (DVT). Further aspects of the method include: pretreating before exposure to prevent the coronavirus and post-infection treating the patient using N-acetyl cysteine (NAC) approximately 600 to 3000 milligrams (mg) daily to achieve at least one of the group consisting of: improve immuno-surveillance in sensing the coronavirus pathogen, to protect patient organs from failure caused by reactive oxygen species (ROS) of inflammation, to enhance IFN-induced gene expression of antiviral proteins, and to reduce the risk of cytokine storm by inhibiting mammalian target of rapamy-cin (mTOR). Further aspects of the method include: pretreating with vitamin D3 approximately 2000 to 5000 international units (IU) daily to boost the patient's innate immune system. Further aspects of the method include: treating with at least one from the group consisting of: statin to reduce cardiovascular risks, statin plus eicosapentaenoic acid (EPA) at 2 grams twice daily to reduce cardiovascular risks, and Diosmiplex approximately 630 mg one to three times daily to improve circulation and to reduce inflammation for endothelial protection.

Further aspects of the disclosure include a method for treating post-viral chronic fatigue with at least one from the group consisting of: a serotonin-norepinephrine reuptake inhibitor (SNRI) such as duloxetine, venlafaxine, and a milnacipran or antiepileptic drug such as gabapentin, pregabalin, lidocaine, topiramate, and carbamazepine for pain; a tricyclic such as nortriptyline and amitriptyline for sleep improvement and pain; a muscle relaxant such as tizanidine, baclofen, and cyclobenzaprine; a systemic corticosteroid such as fludrocortisone for neurally mediated hypotension; and intermittent pulse of prednisone for severe flare-up.

BRIEF DESCRIPTION OF THE DRAWINGS

FIG. 1A shows a normal immune response to pathogen.
FIG. 1B shows an abnormal immune response with hyper-inflammation and cytokine storm.

FIG. 2 is an overview of the Coronavirus Disease 2019 (COVID-19) timeline, stages, symptoms, therapy and treatment methods based on the response of immune system and the disease progression due to Severe Acute Respiratory Syndrome-Coronavirus 2 (SARS-COV2) viral infection.

DETAILED DESCRIPTION OF THE DISCLOSURE

In December of 2019, a novel coronavirus, named Severe Acute Respiratory Syndrome-Coronavirus 2 (SARS-COV2), was found in Wuhan, China. This coronavirus causes the coronavirus disease 2019 (COVID-19) infection in humans. Within a few months it rapidly became a pandemic. By the middle of October 2020, the COVID-19 has caused over 39 million infections and more than 1.1 million deaths worldwide. The number of people who have actually had the virus is likely much higher due to the inadequate testing and asymptomatic cases. There is a strong demand of effective therapy using novel agents and/or repurposed drugs to treat COVID-19 and to reduce the mortality rate.

The presenting symptoms of COVID-19 include fever, dry cough, diarrhea, headache, loss of smell and taste. According to the report on the first 1099 patients from Wuhan published in the New England Journal of Medicine, fever may not be a presenting symptom in more than 50% of hospitalized patient even those who later develop serious complications. Cough is a more common symptom affecting 67 to 70% of patients on admission of which only 33 to 35% had productive sputum. On admission to the hospital, shortness of breath was seen in 15% of non-severe and 37% of severe patients. Fatigue was seeing in 37 to 40% of severe patients. Gastrointestinal (G.I.) symptoms such as nausea, vomiting and diarrhea is less common seen in 3.5 to 7% of patients. Abnormal laboratory findings are common, including leukopenia, lymphopenia, thrombocytopenia, elevated C reactive protein (CRP), abnormal liver functions (including aspartate aminotransferase (AST), alanine aminotransferase (ALT), and lactate dehydrogenase, and elevated D-dimer. Abnormal chest computed tomography (CT) were very common (84% of non-severe and 95% of severe patients); abnormal chest radiographs were also common (54% of non-severe and 76% of severe patients).

Increased risks of COVID-19 are hypertension, diabetes, obesity and lung diseases typically have vascular abnormalities. These patients are more prone to develop serious complications, including acute respiratory distress syndrome (ARDS), thrombosis, multi-organ failures, cytokine storm, septic shock and death. The seriously ill patients are often cigarette smokers and vitamin D deficient. These patients with preexisting conditions have high risk factors for COVID-19 complications. They should be moved to the front of the line for close monitoring and early treatment. Elderly adults in particular are highly susceptible to SARS-COV2 infection, due to aging immune system and comorbidities.

COVID-19 is an acute viral infection that can trigger complicated immune system responses depending on the host. Upon the invasion of SARS-COV2, the responses of a host to a virus can be generally categorized into 3 types: resistant host, tolerant host, and susceptible host. A resistant host regains fitness by effectively recognizing and eliminating the virus. A tolerant host is able to reduce the immunopathology and tissue damages inflicted by the virus. A susceptible host is unable to control viral replication and develops excessive immunological reaction, hyperinflammation, resulting in server illness. Due to the persistence of the SARS-COV2 virus and/or triggering of the immune mediated damages, a susceptible host upon infection can rapidly progress to severe status and may ultimately succumb to CoVID-19.

This disclosure discloses immunotherapy methods combining immunomodulatories and antivirals to prevent and to reduce the severity of COVID-19 infection. Successful treatment of COVID-19 requires prevention, early recognition and detection, the ruling out of co-infections, serial laboratory monitoring, and clinical monitoring for worsening and timely treatments. Using this disclosure as preventive, management and therapeutic options for COVID-19, infected patients can be more resilient to viral challenges, recovering faster with less organ damages and adverse residual effects.

FIG. 1A shows a normal immune response to a pathogen. The immune system has two principle mechanisms: innate immunity and adaptive immunity. Upon the exposure to infection, the innate immune mechanism, including epithelial barriers, phagocytes, natural killer cells and complement systems are typically activated within 12 hours. It is followed by the activation of adaptive immunity mechanism in a few days. The adaptive immunity is mediated by lymphocytes and their products. B-cell lymphocytes produce antibodies to block infections and to eliminate the pathogens. T-cell lymphocytes eradicate intracellular microbes. The activation of the immune system is a protective response to an infection or tissue injury that promotes the clearance of pathogens and wound healing. After eradication of the inflammatory stimulus of microbe, multiple mechanisms actively resolve inflammation to restore normal tissue homeostasis. The relationship between the viral replication and spread and lymphocyte activation and expansion determines the outcome of a viral infection. In some cases the inflammatory response fails to subside to a homeostasis level, resulting in persistent and prolonged inflammation which can significantly contribute to the pathogenesis of organ damage.

FIG. 1B shows a sub-optimal immune response with hyperinflammation and a cytokine storm. In some patients, COVID-19 may trigger sub-optimal immune response that is ineffective to clear the pathogens resulting in persistent stimulation that can trigger the hyperinflammation and cytokine storm. It is important to promptly put a break and reset to the over-reactive host immune response to avoid out of control cytokine storm and multi-organ damage and death. Early and prompt treatments will keep the disease in low activities with minimal damages and to prevent run-away inflammation and avoid the deadly consequences of a cytokine storm. A cytokine storm is driven by inflammatory cytokines including tumor necrosis factors (TNFs), interleukin 1 (IL-1), interleukin 6 (IL-6) and vascular endothelial growth factors. The pre-exposure prophylaxis and post-exposure prophylaxis disclosed herein are two key components of comprehensive methods disclosed herein to prevent serious COVD-19 disease progression to cytokine storm and the dreaded consequences. COVID-19 disease is a complex interplay between the virus SARS-COV2 and the host's immune system. Studies of other viral infections have shown the antiviral treatment alone was less effective than in combination with immunomodulatory therapy. The goal is to develop a comprehensive therapy to block virus entry and/or replication and immunomodulators that target the immune cascade in a timely manner. Depending on the stages of COVID-19 infection, different immunomodulatory and anti-inflammatory therapies can be applied timely in addition to antiviral treatments. Antivirals work the best when used at the early onset of the diseases. However, the pathology of severe viral infection is mediated by host-factor cytokine responses and not necessarily by a viral load per se.

FIG. 2 is an overview of the COVID-19 therapy and treatment methods based on the response of the immune system and the disease progression to a SARS-COV2 viral infection. The stages of infection and the treatment methods are guided by clinical history, symptoms, laboratory tests and biomarkers monitored regularly as outpatient or daily as an inpatient. The complex interaction between the virus and the host responses determines the outcome of COVID-19 infection and thus a combinational therapy treating the virus and treating the host would be more effective than either monotherapy alone. The synergistic treatment of immuno-modulator and antiviral will yield the best outcome. Preconditioning for the SARS-COV2 Pandemic.

First of all, treat to target of baseline co-morbidities such as diabetes, hypertension, obesity and lung disease. Stopping cigarette smoking is another important aspect of preventing a COVID-19 infection. Cigarette smoking extracts and inhibits retinoic acid-inducible gene I (RIG-I) that is a major sensor of the host to detect and mount antiviral responses against a ribonucleic acid (RNA) virus. It is never too late to add lifestyle modifications to improve co-morbidities. In the seriously ill patients those taking statins have 40% lower mortality which is potentially due to endothelial cells stabilization. Patients with rheumatic diseases should continue their immunosuppressive and biologic treatments to minimize inflammation and to prevent flare-ups. Vitamin D is important to boost the innate immune system. The relative risk of Covid-19 may increase by 77% with vitamin D deficiency. There is also an association between low vitamin D concentration and high rates of COVID-19 infection and death. Vitamin D is needed by the response of innate immunity such macrophages to defend against the invasion of a virus and bacteria. In addition, Vitamin D is important in modulating cellular immune responses and attenuating cytokine storm. The activated form of vitamin D enhances the immune response is supported by joint guidance by multiple medical societies around the world in the era of COVID-19. The seriously ill COVID-19 patients are often vitamin D deficient. Compared to 400 to 1000 international units (IU) daily that are used for building a stronger skeleton and to prevent bone loss, COVID-19 patients should use higher dosage: 2000 IU daily of vitamin D3 aiming for levels of 50 to 60 nanograms per milliliter (ng/ml). The normal range is 30 to 100 ng/ml in most US laboratories.

Since the SARS-COV2 virus is mainly transmitted by aerosol and droplets, masks, social distancing and avoiding large gathering is essential to prevent the spread of COVID-19 infections. SARS-COV2 gains cellular entry through angiotensin-converting enzyme 2 (ACE2) surface receptors, which are normally expressed by diverse human cells. ACE2 receptors are highly expressed in nasal cavity, oral mucosa, lungs, and endothelial cells and therefore masks should be worn to decrease viral inoculum. The infection of endothelial cells by SARS-COV2 can cause endothelial dysfunction, predisposing to vasoconstriction, inflammation, and thrombosis. As ACE2 receptors are also expressed in the small intestinal epithelial cell up to 20% of patients may have diarrhea. The gastrointestinal tract has billions of microbiome which is considered the second immune system. Therefore, it is good to cultivate a healthy microbiome ecosystem in the intestines with probiotic and prebiotic to help protect the gastrointestinal (GI) endothelial cells.

When the influenza season arrives in the fall and winter, co-infection with COVID-19 will turn an already desperate pandemic into a disaster. The best prevention of the influenza is immunization. Therefore everyone should be vaccinated, especially the elderly and the patients with comorbidities. When influenza is in season, hospitals should check for the possibility of co-infection with influenza with rapid tests for influenza. Oseltamivir should be begun within 24 hours of fever, body ache or cough. If bacterial co-infection is suspected, appropriate antibiotics should be initiated. The patient should be switched to narrow spectrum antibiotics when culture and sensitivity results are available. Bacterial co-infection was responsible for the majority of fatal or life-threatening pneumonia during the 1918 influenza pandemic. More recently, *Streptococcus pneumoniae* bacteria infections impaired the immune response of patients during the H1N1 virus pandemic in 2009. Therefore, during the COVID-19 pandemic pneumococcal vaccination, as well as influenza vaccination, should be expanded to include all adults. Supported treatments such as oxygen, putting the patient in a prone position, and low tidal volume ventilatory support may also be considered.

Pretreating

In this disclosure, "pretreating" is defined as initiating the treatment before the exposure to virus, infection, or appearance of symptoms and the continuation of the treatment afterwards, or initiating the treatment after the occurrence of viral exposure, infection, and symptoms if the treatment has not been started already. N-acetyl cysteine (NAC) can be used as prophylaxis for COVID-19. NAC is an endogenous compound that is made from the amino acid L-cysteine. NAC acts as a scavenger for reactive oxygen species (ROS). It is a substrate for the synthesis of glutathione (GSH) in the liver which is an important anti-oxidant with a number of roles throughout the body. It has been implicated for protecting the organs from oxidative damage by reducing inflammation during viral infection. NAC improves immunosurveillance by which the immune system recognizes foreign pathogens such as virus, bacteria, and/or cancerous cells. NAC has been shown to restore retinoic acid-inducible gene (RIG-I) virus sensing capability. RIG-I is an essential molecule in the immune system for recognizing cells that have been infected by viruses including the coronavirus. Once RIG-I is triggered by double stranded RNA (dsRNA), the signal cascades by caspase activation and recruitment domains (CARDs) and mitochondrial antiviral signal proteins (MAVS). The signal then activates human interferons (IFNs) antiviral gene expression to limit the virus spreading to nearby cells, to promote innate immune response and to help activate the adaptive immune system. With its antioxidant property, NAC can improve immune response by reducing the oxidative stress (e.g., due to advanced age and pre-existing conditions) which impairs IFN-induced gene expression for antiviral proteins. For influenza, NAC taken during flu season has been shown to decrease flu symptoms from 79% to 25%. NAC also synergistically improves the antiviral effectiveness of oseltamivir against the influenza. When NAC is given at the early onset of a cytokines storm, it can prevent progression to acute respiratory failure, septic shock and multi organ failure. NAC is an inhibitor of mammalian target of rapamycin (mTOR) which is the pro-inflammatory pathway implicated for cytokine storm. The suppression of the mTOR nucleotide-binding domain leucine rich NLR family pyrin domain containing 3 (NLRP3)- interleukin 1 beta (mTOR-NLRP3-IL 1Beta) axis can prevent cytokines storm and the subsequent hypoxemic respiratory failure and multiple organ failure. The pretreatment or immediate post-exposure treatment with NAC at the onset of COVID-19 symptoms is critical, since the onset of acute respiratory distress syndrome (ARDS) and cytokines storm can develop abruptly. Unfortunately, 80% of COVID-19 infection is asymptomatic, or mild, therefore the timing of treatment may be tricky. By pretreating with NAC, which is an mTOR inhibitor, before COVID-19 infection, the risk of cytokine storm can be reduced or averted. NAC has multiple medical indications as a specific antidote for acetaminophen overdose, prevention of chronic obstructive pulmonary disease exacerbation, and prevention of contrast induced kidney damage. NAC's mucolysis property is advantageously used in the management of chronic obstructive pulmonary disease. It is noted that NAC's plays a number of roles throughout the body and has been implicated for slowing the aging process, protecting internal organs from oxidative damage, and reducing inflammation. NAC may also possibly reduce the risk for numerous diseases including cancer, may be a cancer chemoprentive, an adjunct in the eradication of *H pylori* and prophylaxis of gentamicin induced hearing loss in patient on renal dialysis.

During systemic inflammatory response syndrome (i.e., septic shock), endothelial damage and multiple organ failure may result from reactive oxygen species (ROS). Glutathione (GSH) is one of the most important endogenous antioxidants. NAC is a precursor of GSH and acts as scavenger for ROS. Patient with early septic shock who received NAC and GSH showed a significant decrease in peroxidative indexes and an improvement of the clinical score. Clinically, oxidative stress and inflammation can induce mucin gene expression leading to mucin production. In addition to reducing oxidative stress and inflammation, NAC is mucolytic by reducing mucin gene expression and mucin production. NAC alters the secretion of mucus and its physical properties, resulting in improvement of mucociliary clearance. It has been used for exacerbation of chronic bronchitis, as NAC synergistically works with antibiotics. SARS-COV2 attacks the alveolar cells of the low respiratory track. NAC inhibits mucin synthesis and pro-inflammatory mediators in alveolar type II epithelial cells, infected with influenza virus A and B and with respiratory syncytial virus (RSV). NAC has been shown to attenuate illness from multiple virus, including influenza A and B, RSV, rhinovirus, HIV and Coxackievirus-B. Attenuation of influenza-like symptomology and improvement of cell mediated immunity may be obtained with long-term NAC treatment. With NAC prophylaxis 600 mg taken twice a day for 6 months, only 25% of virus-infected subject develop symptoms versus 79% in a placebo controlled study. This study has shown that taking NAC during flu season decreased flu symptoms from 79% down to 25%.

As a result of bacterial or viral infection, pulmonary inflammation results from the host immune responses that produce cytokines, chemokins and reactive oxygen species (ROS). These chemicals contribute to pulmonary damage, organ failure and acute respiratory distress syndrome (ARDS). Animal studies showed that NAC synergistically enhances oseltamivir in protecting mice from lethal influenza infections. Survival was 100% in mice treated with NAC+oseltamivir versus 60% with oseltamivir alone, or 20% with NAC alone. Recent research indicates that NAC decreases phosphorylation of signal transducer and activator of transcription 3 (STAT3) and down regulate janus kinase 2 (JAK2) and janus kinase 3 (JAK3). NAC basically acts as a JAK inhibitor and decreases transcription of pro-inflammatory genes. NAC can also reduce inflammation of systemic lupus erythematosus (SLE) by blocking mTOR in T-cell lymphocytes.

Although COVID-19 is generally known to cause respiratory illness, the virus can be disseminated by viremia via bloodstream to cause damages throughout the body. Virus along with over-reacting immune system can also damage other organs including heart, intestinal tract, kidneys, and the brain. COVID-19 patients with severe infection are known to die from strokes and heart attacks. In vivo studies, NAC effectively alleviates Coxackievirus B-Induced myocarditis through suppressing viral replication and inflammatory responses. The Middle East Respiratory Syndrome coronavirus (MERS-COV) can cause acute myocarditis and heart failure. COVID-19 infection also causes acute myocardial injury and chronic damage to the cardiovascular system. The patients with severe symptoms admitted to the intensive care unit (ICU) often have complications. These complications may involve acute myocardial injury with increased high sensitivity cardiac troponin levels (cTnI) and biomarkers of myocardial injury and elevated creatinine kinase myocardial bands (CK-MB). CK-MB is found specifically in the heart muscle and high level of CK-MB means damage in the heart.

Some patients have presented with heart palpitations and chest tightness rather than with respiratory symptoms, such as shortness of breath (dyspnea) and cough, but were later diagnosed with COVID-19. It was reported that a patient died of a "massive heart attack", epicardial hemorrhage, which was later identified to be the earliest COVID-19 case in the United States. Among the people who died from COVID-19, it has been reported that 11.8% of patients without underlying cardiovascular disease (CVD) had substantial heart damage, with elevated levels of cardiac troponin I (cTnI) or cardiac arrest during hospitalization.

N-acetyl cysteine (NAC) is an immunomodulator which is an inhibitor of viral replication, a suppressor of cytokine dysregulation and enhancer of adaptive immunity during viral infection. NAC increases GSH which is an anti-oxidant which protects organs from reactive oxygen species (ROS) and inflammation damages. NAC decreases phosphorylation of signal transducer and activator of transcription 3 (STAT3) and down regulate janus kinase 2 (JAK2) and janus kinase 3 (JAK3) and decrease transcription of pro-inflammatory genes. NAC is a mucolytic which works synergistically with antibiotics and antivirals to treat bronco-pulmonary infections. NAC is an mTOR inhibitor to prevent cytokine storm and its consequences. NAC is inexpensive and well tolerated. It can prime various organs in the body ready to defend the systemic attack by SARS-COV2. It therefore should be broadly adopted as the pretreatment for dosage at approximately 2 gram/day, 600 mg for 3 times/day, or 1000 mg for 2 times/day before COVID-19 infection. NAC properties protect organs form oxidative damage, modulate the immune system, inhibit the viral replication, reduce inflammation, prevent cytokine dysregulation i.e., onset of a cytokine storm, and enhance adaptive immunity during viral infections. It should be taken throughout the COVID-19 pandemic period.

Viral load is a measure of viral particles present in an individual. It is determined by the amount of infectious dose (viral inoculum) and the rate of viral replication within the host. The viral load may impact on the magnitude and quality of the host's T-cell response and its cascade to trigger a cytokine storm. Evidence suggests an association of viral doses with the severity of COVID-19 disease. A viral load is higher in patients who have more severe COVID-19 disease. It is imperative to have the lowest viral load to prevent overreaction of the host immune system resulting in overwhelming hyperinflammation, tissue damage, multi organ failure, respiratory failure, septic shock and death. Reducing the intensity and frequency of exposures to SARS-COV2 can reduce the infectious dose and thus less viral load and less severe cases.

Post Exposure Prophylaxis

The blocking of virus cellular entry and replication thus preventing further spread to other host cells is the essential initial step to lower the viral load. The SARS-COV2 coronavirus can rapidly multiply in an exponential manner. It can enter-replicate-exit a host cell in a 10 hours cycle, releasing several hundred new copies of virus to further spread the infection. Given the speed of virus replication, early treatment is critical in battling SARS-COV2. The pre-exposure preventative NAC treatment and the early post-exposure prophylaxis with hydroxychloroquine (HCQ) is important in preventing the severity progression of COVID-19 infection. The SARS-COV2 coronavirus invades the human body via angiotensin converting enzyme-2 (ACE2) receptors, found in high concentrations in the lung's alveolar epithelial cells, kidney, cardiovascular system and the gastrointestinal system's small intestinal epithelial cells. Hydroxychloroquine (HCQ) interferes with the ACE2 receptor glycosylation which is necessary for the virus-cellular receptor binding, the first step of infection. Furthermore, HCQ is an endosomal acidification inhibitor. HCQ is also a weak base which can easily enter and accumulate in the cytoplasmic vesicles. The higher pH of cellular endosomes from 4.0 to 6.0 stabilizes lysosomal membrane, interferes with the virus and host cell fusion, and decreases the efficiency of viral entry, replication and infection. HCQ's exhibits additional benefit in decreasing thrombocyte aggregation. It is critical to begin HCQ as soon as possible after exposure to SARS-COV2 even if the patient is asymptomatic as seen in 80% of the patients. The usual dose of HCQ is 200 mg twice a day and a loading dose of 400 mg twice a day may be added to quickly increase plasma levels of the drug.

HCQ was originally used to treat malaria which causes systemic inflammation. For more than 60 years, it has been used to treat rheumatoid arthritis, lupus and other connective tissue diseases. HCQ has five proven effects for lupus, including treatment of active disease with over-active inflammation, reduction of the frequency of flares, prevention of venous and arterial thrombosis, protection against neonatal heart block, and reduction of mortality. HCQ has a long track record in safety. It is one of the safest Disease Modifying Anti-Rheumatic Drugs (DMARD'S) available and it is prescribed to pregnant women and children. However, it should be avoided using HCQ together with drugs which could prolong QT interval including erythromycin, azithromycin, or lopinavir-ritonavir (LPV-RTV) as it may cause the adverse effect of increased QT interval. The QT interval is the measurement made on an electrocardiogram used to assess some of the electrical properties of the heart and severe long QT interval may lead to dizziness, fainting, and even cardiac arrest.

It is noted that glucose-6-phosphate dehydrogenase (G6PD) deficiency should be checked before using HCQ. Decreased production of G6PD results in deficient levels of nicotinamide adenine dinucleotide phosphate and reduced GSH causing oxidative stress and red blood cell destruction. Patients may develop hemolytic anemia triggered by certain infectious agents and medications. For G6PD deficient patients, HCQ can increase the risks of hemolytic anemia and should be replaced with other antiviral as the first line of defense. NAC should be used especially for G6PD deficient patients to maintain GSH to reduce the oxidative stress.

D-dimer is a fibrin degradation product which is a small protein fragment present in the blood after a blood clot is degraded by fibrinolysis. Elevated D-dimer indicates recent or ongoing intravascular coagulation and fibrinolysis and is frequently seen in hospitalized COVID 19 patients. As HCQ is known to prevent venous and arterial thrombosis in lupus patients, it is an added benefit in treatment of COVID 19 patients with early (i.e., within day 1 to day 7 of symptoms), and mild to moderate disease. The side effect in long-term use of HCQ is retinal toxicity. Retinal toxicity is seen in 1.8% of patients after 6 years, 3.3% after 11 years, and 11.5% after 16 years. The current recommendation by the American College of Ophthalmology is that after a baseline evaluation, a second eye exam is not required for 5 years unless there are unusual risk factors. Considering the acute nature of COVID-19 disease, the retinal toxicity risk of HCQ is very low.

Protease inhibitors such as nafamostat and camostat have strong inhibitory actions against transmembrane protease serine 2 (TMPRSS2) enzyme to prevent the activation of S-protein on the SARS-COV2 virus to gain entry to the host cells thru ACE2 receptors. Both can be used as a post-exposure prophylaxis for COVID-19 with an added benefit as an anticoagulant. They can prevent viral replication and prevent further spread of virus to other cells. Nafamostat or camostat can be used in combination with antivirals such as lopinavir-ritonavir, favipiravir and remdesivir. An important element of the treatment is to prevent acute respiratory distress syndrome (ARDS) usually seen around day 10 to 12 from onset of initial symptoms especially in the elderly, those with co-morbidities and serious symptoms. Hypoxia is a sign of severe acute respiratory syndrome in COVID-19 with lung involvement. Higher levels of oxygen after oxygen supplementation may be associated with reduced mortality rate. Oxygen saturation ($SpO_2$) at 90.5% cutoff value is a good prediction of survival based on a retrospective study. In the clinical course of COVID-19 lung involvement, dyspnea is usually seen by day 4 to day 7; intubation is usually by day 15; and death by day 19.

Lopinavir-ritonavir (LPV-RTV) is a combination of 2 protease inhibitors used as antiretroviral for HIV infection. Lopinavir inhibits coronavirus main proteinase 3C-like protease protein (3CLpro). It prevents the virus from reaching its mature state thus preventing infection. It is metabolized by cytochrome P4503A (CYP3A) enzymes in the liver. Thus, a CYP3A inhibitor (e.g., ritonavir) is added to this combination drug to decrease metabolism and increase drug bioavailability for lopinavir. Because this combination is involved with the CYP3A enzyme system, a drug-drug interaction is expected, and it is necessary to closely monitor patients who are on other CYP3A4 substrates to prevent unintended toxicity. LPV-RTV can exhibit anti-SARS-COV2 activities. This combination drug should be considered early, preferably with onset of cough or shortness of breath COVID-19 symptom onset.

At the onset of dyspnea at around day 4 to day 7 after the initial onset of symptoms (either as inpatient or outpatient) the patient should be treated with LTP-RTV 200/50 at 2 tablets twice a day, as a first-line defense before costly ICU or intubation. LPV-RTV should not be used in combination with HCQ as it may cause serious arrhythmia such as increased QT interval and death.

Favipiravir is another antiviral that can be used to treat COVID-19. Originally, developed for treating influenza, favipiravir targets RNA-dependent RNA polymerase (RdRp) enzymes which are necessary for the transcription and replication of virus. For better results, it should be used early (i.e., day 3 to day 9 or earlier) for those present with dyspnea, hypoxemia and pneumonia. It should be used for 5 to 10 days. However, favipiravir should not be used for pregnant woman.

Remdesivir, is yet another RdRp antiviral which has shown to decrease length of hospitalization. Again, remdesivir should be used early since onset of symptoms, in those present with dyspnea, hypoxemia, and pneumonia. It should be used for 5 to 10 days.

In general, the antivirals mentioned above including nafamostat, camostat, LPV-RTV, remdesvir, and favipiravir are preferably used at an early stage of the infection to block the viral replication and spread. By the time the patient presented with acute respiratory distress syndrome (ARDS) or is intubated (typical day 10 to day 15) the SARS-COV2 virus has already won the battle. Drug-related heart damage during COVID-19 treatment is a concern. In particular, the use of antiviral drugs should be monitored. In a study of 138 patients with COVID-19, 89.9% were given antiviral drugs. However, many antiviral drugs can cause cardiac insufficiency, arrhythmia or other cardiovascular disorders. Therefore, during treatment of COVID-19, especially with the use of antivirals, the risk of cardiac toxicity must be closely monitored. Severe cases of COVID-19 are associated with lymphopenia, neutrophilia, thrombocytopenia and coagulation defects. Clinical and laboratory markers can be used to optimize treatment COVID-19 early and regular blood test monitoring may signal development of serious COVID-19 disease.

A key objective is to timely reset and put a break on the hyper-inflammatory reaction due to the inappropriate host response causing an out of control cytokine storm. If the host response is excessive, hyper-inflammatory reaction will result in tissue damage and fibrosis. In the severely ill COVID-19 patients, the resulting cytokine storm causes acute respiratory distress syndrome (ARDS), septic shock and multiple organ damage.

Lymphopenia is a marker for T-cell dysfunction and pending immune system dysregulation, prompt antiviral treatment with oral LPV-RTV or intravenous (IV) remdesivir is critical to prevent further immune system deterioration.

The D-dimer test helps diagnose thromboembolism caused by COVID-19. The normal value of D-dimer is less than 0.5 micrograms per milliliter (mcg/ml). When a blood clot is dissolved in the body, a protein fragment called D-dimer is produced. It is a highly sensitive in diagnosing acute deep venous thrombosis, pulmonary embolism, or clotting caused by endothelia dysfunction. Elevated D-dimer occurs after blood a clot has formed and the clot is in the process of breaking down. The initial thromboembolism may migrate to other sites resulting in multi organ failures. Elevated D-dimer was found in 43 to 66% of hospitalized COVID-19 patients. Therefore, early detection of an above normal D-dimer value is critical. Anticoagulation is mandatory, if D-dimer is found above the normal value. Depending on the level of D-dimer, anticoagulation including heparin, warfarin, enoxaparin sodium, acetylsalicylic acid, clopidogrel, or direct oral anticoagulants such as apixaban, dabigatran, rivaroxaban, and edoxaban may be used.

Many COVID-19 patients have elevated high sensitivity cardiac troponin I (hs-cTnI) or the creatinine kinase (CK- MB) indicating myocardial injuries. Monitoring in the hospital for acute myocardial infarction, arrhythmia, hypertension, hypotension or septic shock is critical.

Biologic treatments such as tumor necrosis factor (TNF) inhibitors, Interleukin-1 (IL-1), Interleukin-1 beta (IL-1 beta) receptor antagonists, and interferon B, should be considered in an anti-inflammatory strategy to combat COVID-19. In particular, TNF is a major component of inflammatory cytokine secreted by macrophage and many other types of cells. Biologic TNF inhibitors are fast-acting in TNF reduction. The blockage of TNF can also lead to rapid down regulation of other pro-inflammatory cytokines including IL-1, interluekin-6 (IL-6) and granulocyte-macrophage colony stimulate factor (GM-CSF). In addition, it can also rapidly reduce elevated D-dimer and coagulation factors. Anti-inflammatory TNF-inhibitors can be used on the early signs of lung function deterioration. A TNF-inhibitor is synergistic with antivirals. TNF-inhibitors include infliximab, etanercept, adalimumab, certolizumab, and golimumab. They are available in either intravenous (IV) therapy or subcutaneous therapy. While inflammatory mediators involved in cytokine storm include TNF, IL-1, Interluekin-10 (IL-10), Interleukin-18 (IL-18), and GM-CSF. TNF inhibitors can be used as a first line treatment to prevent emerging hyper-inflammation and a cytokine storm. In addition, a TNF inhibitor is a cost-effective treatment choice for COVID-19 due to the recent introduction of multiple biosimilars.

During the advanced stage of COVID 19 infection, the patient's own immune system can cause a cytokine storm which results in serious illness such as acute respiratory distress syndrome (ARDS); multi-organ failure, thrombosis, septic shock and death. The new paradigm requires changes to combat inflammation and modulate cytokine expression. The median time until development of pneumonia is between 4 to 5 days after onset of COVID-19 symptoms. Therefore the patient should be monitored closely for shortness of breath, oxygen desaturation, and laboratory studies for early signs of pneumonia, ARDS and a cytokine storm.

A predictor of COVID-19 ARDS is elevated Interleukin-6 (IL-6). Elevated IL-6 due to COVID-19 can be treated with an IL-6 inhibitor. Patients frequently present with elevated C-reactive protein (CRP) due to elevations in IL-6. Tocilizumab and sarilumab are two commercially available IL-6 receptor agonists. Physicians should consider these IL-6 inhibitor biologic treatments prior to transfer to ICU and intubation. Since both medications are available as subcutaneous self injections, therefore, they may be administered as outpatient treatments. However, if patients present with high CRP, shortness of breath, decreasing oxygen saturation (<92%), then hospitalization is imminent.

In the lungs, respiratory epithelial cells and alveolar macrophages will die after infection by the COVID-19 virus. Acute inflammatory responses occur when pathogen-associated molecular patterns (PAMPs) of invading virus and damage-associated molecular patterns (DAMPs) of damaged cells are recognized by the pattern recognition receptors (PRRs) of innate immune cells. This will result in the activation of pro-inflammatory cytokines and recruitment of inflammatory cells. In a meta-analysis from seven studies originated from China, IL-6 elevation was 2 to 4 times higher in the severely ill compared to the non-severe COVID-19 patients.

The hepatic synthesis of the acute phase reactant, CRP, is induced by plasma cytokine interleukin 6 (IL-6) secreted by macrophage and T cells. While low-grade inflammation shows only minor CRP elevation, acute inflammation generally shows a marked CRP response. High CRP levels are a key inflammatory marker for a cytokine storm. Elevated CRP is found in more than 50% of hospitalized COVID-19 patients. CRP tests are widely available and inexpensive tests providing a good measure of IL-6 level indirectly. Another measurement of acute phase protein would be erythrocyte sedimentation rate (ESR). Prompt initiation with IL-6 receptor inhibitor as outpatient or inpatient is critical to avert impending cytokines storm, respiratory failure and intubation. Thus CRP is an optimal biomarker for early identification of potential impending COVID-19 cytokine storm. Markedly elevated levels of CRP are strongly associated with infections. CRP can be found in bacteria or virus infected patients in excess of 5 to 10 times above the upper limit (typically 8 or 10 mg/liter) of the normal value. Since CRP could be elevated in patients with either viral infections or bacterial infections, bacterial and other viral infections should be identified with a fever work-up including blood urine culture, chest x-ray, and influenza rapid testing and then properly treated.

Bio-markers including D-dimer, lymphocyte counts, IL-6, and cardiac troponin-1 should be monitored from the onset of illness. From the early stage (4 to 7 days or earlier), the deviations and the trend of these markers are correlated to the groups of survivors versus non-survivors. In particular, patients that are prone to progress to serious stages and mortality can be detected early based on elevated D-dimer, IL-6, cardiac troponin-1, and decreased lymphocyte count. Elevated D-dimer indicates thromboembolic events which may lead to multi organ failure, therefore early detection and anticoagulation is necessary. The normal value of D-dimer is about 0.5 micrograms per milliliter (mcg/ml). D-dimer 2.5 mcg/ml or five times of the normal value should raise red flags for closer daily monitoring. If D-dimer continues to increase, then anticoagulation treatment using an anticoagulant such as heparin, warfarin, enoxaparin sodium, acetylsalicylic acid, clopidogrel, or direct oral anticoagulants (DOACs) should be initiated to keep blood clots from forming in arteries, veins, heart, brain, and other parts of the body. Traditional anticoagulants such as warfarin require closely monitored international normalized ratio (INR) blood test and dietary consideration to avoid uncontrolled bleeding. DOACs such as apixaban, dabigatran, rivaroxaban, and edoxaban are highly effective and requiring less monitoring.

Immunotherapy using a biologic immunomodulator is important to the success of treating Covid-19 patients. If IL-6 is greater than 7 picograms per milliliter (pg/ml), then it is an indicator to launch IL-6 inhibitor in order to reduce the risk of over-reacting inflammation, a cytokine storm and to improve survival. IL-6 inhibitors including tocilizumab and sarilumab are available in subcutaneous (SubQ) injection and can be administered outside of a hospital facility. Alternatively, TNF-inhibitors including infliximab, etanercept, adalimumab, certolizumab, and golimumab can be used, since the blockage of TNF can lead to the rapid down-regulation of IL-6. CRP is a reflection of IL-6 which is a cytokine correlated with disease severity. Along with symptoms of dyspnea or hypoxia, CRP should be monitored frequently at the onset of COVID-19 infection.

Hyperinflammation (defined as CRP>50 mg/L) is present with patients in serious SARS-COV2 infections, bilateral pneumonia, and respiratory failure requiring supplemental oxygen. Elevated CRP is a marker for an impending cytokine storm, and the patient should be treated very aggressively with a biologic immunomodulator and antiviral to prevent intubation and ICU admission.

If CRP is elevated above 30 mg/L, a biologic immuno-modulator such as TNF-inhibitors including infliximab 3 to 5 mg/kg intravenous (IV), etanercept 50 mg SubQ, adalimumab 40 mg SubQ, certolizumab 400 mg SubQ, and golimumab 50 mg SubQ or 2 mg/kg IV; IL-6 inhibitors including tocilizumab 8 mg/kg, and sarilumab 200 mg SubQ; or inflammasome pathway related inhibitors including NLRP3 inhibitors dapansutrile (oral, topical, or inhalable) and colchicine (0.6 mg once to twice a day), IL-1 beta inhibitor canakinumab 300 mg SubQ, and IL-1 inhibitor anakinra; should be used as soon as possible to prevent progress in severity. Additional dosages may be given pending patient response.

Elevated high sensitivity cardiac troponin-1 indicates on-going cardiac damage. It is correlated with cardiac infarction size. The normal value of high sensitivity cardiac troponin-1 is 0 pg/mL and any detectable elevation is significant. If left untreated, it can lead to permanent cardiac damage, morbidities, disabilities and death. After treating the underlying acute COVID-19 infection with immuno-modulator plus antiviral plus anticoagulation is successfully accomplished, then T-cell immunosuppressant such as cyclosporine, tacrolimus, sirolimus, and mycophenolate should be considered for any residual or on-going cardiac damage. After discharged from hospitalization, patients should be monitored for cardiovascular conditions and treated with statins or statins plus eicosapentaenoic acid (EPA) as indicated.

Infection of macrophages and lymphocytes is a key component of COVID-19 induced pathogenesis. COVID-19 infects T-cells contributing to lymphopenia. Leukopenia and lymphopenia may be due to T-cell senescence indicating the body's immune system is exhausted and at high-risk of impending cytokine storm as a last ditch effort by the immune system. A lymphocyte count below $800 \times 10^6$/mL is an early indicator of fragility and increased risk of mortality. Immunotherapy and antiviral should be immediately launched.

The patients with shortness of breath, dyspnea, on exertion, chest pain and a partial pressure of oxygen ($PaO_2$) less than 93% are at a higher risk of developing ARDS and should be admitted to the hospital. These patients should be treated very aggressively with antivirals such as LPV-RTV, nafamostat, camostat, remdesivir, or favipiravir and an immunomodulator such as TNF inhibitor, IL-6 inhibitor, or inflammasome pathway related inhibitor (e.g., NLRP3 inhibitor, IL-1 beta inhibitor, IL-1 inhibitor) and started on NAC 1000 mg twice a day if not already on board.

Many risk factors for severe COVID-19 are vascular related such as hypertension, diabetes and obesity. These comorbidities cause pre-existing damage to the blood vessels, since the ACE 2 receptors for COVID-19 virus attachment are abundant both in the lungs and in the lining of the heart and blood vessels. Many COVID-19 patients have elevated high sensitivity cardiac troponin-1 (hs-cTn1) or the creatinine kinase (CK-MB) indicating myocardial injuries. Significantly higher blood pressure is seen in COVID-19 infected ICU patients as well as arrhythmia, acute myocardial infarction, and septic shock. In the U.S., the Centers for Disease Control and Prevention (CDC) has reported that in patients infected with COVID-19, nearly ⅓ have diabetes and ½ have pre-existing hypertension.

A study in Germany found that 78% patients have residual left ventricular dysfunction and ongoing inflammation even more than two months after recovered from the COVID-19 infection. Surprisingly, 67% of them were outpatients indicating that they had only mild symptoms and never hospitalized.

In a report on 39 autopsies of COVID-19 patients who died from pneumonia, acute viral replication and high viral load were seeing in 66.7% of the heart examinations without acute myocarditis. This is evidence of direct viral infection of the heart by COVID-19. In another report, right ventricular dilatation is the most frequent echocardiographic abnormality in COVID-19 patient, likely due to pulmonary parenchymal or vascular disease. These studies indicate significant portion of patients may have ongoing myocardial damage after recovering from seemingly mild symptoms. Therefore monitoring on a regular basis is necessary to prevent long-term cardiovascular consequences of COVID-19. After recovery for COVID-19, patients should be monitored for cardiovascular conditions and treated with statins or statins plus eicosapentaenoic acid (EPA) as indicated.

Weekly high sensitivity cardiac troponin-1, CPK-MB, CRP, and D-dimer should be monitored for the recovered sub-acute and chronic COVID-19 residuals. More frequent monitoring and cardiac magnetic resonance imaging (MRI) is warranted depending on levels of abnormality, disregarding COVID-19 severity or lack of cardiovascular symptoms. Convalescent immunoglobulin derived from recovered COVID-19 patient has shown to improve the seriously ill patients. If availability permits, early treatment may be offered. The janus kinase (JAK) inhibitors such as tofacitinib, baricitinib, upadacitinib, and filgotinib, can also be used. However, JAK inhibitors may cause thromboembolic side effects, and should be avoided in patients with elevated D-dimer.

Glucocorticoids such as dexamethasone may reduce the mortality in COVID-19 patients presented with acute respiratory distress syndrome (ARDS). Dexamethasone has benefit for hospitalized critically ill patients with excessive inflammation who need ventilators or supplemental oxygen alone. The chronic use of steroids has risk for serious adverse events including cardiovascular disease, osteoporosis, and diabetes. It is noted that short term use of steroids can also cause many adverse events. In a large scale observation study in Taiwan, 2.6 million patients of various diseases who received short bursts of steroids for up to 14 days with a median duration of 3 days. These patients were associated with greater risk for gastrointestinal bleeding, sepsis and heart failure with incidence rate ratios (IRRs) of 1.80, 1.99 and 2.37 respectively. In United Kingdom, 5 times sepsis and 3 times thromboembolism and 2 times fractures within 30 days of starting steroid treatment. Therefore, steroid treatment for COVID-19 should be limited in the hospitalized critically ill with respiratory failure needing ventilator or supplemental oxygen.

11.8% of COVID-19 deaths showed cardiac involvement in those without previous cardiovascular disease. 78% of COVID-19 convalescent patients showed abnormal cardiac magnetic resonance (MR) of which ⅔ have only mild symptoms. End organ damage may occur due to virus invasion, host response to body damage, hyperinflammation or blood clots. Elevated D-dimer is an indication of host response to blood clots which is a breakdown product of fibrinolysis. Blood clots, while necessary to stop bleeding, may lead to complete blockage of blood flow, leading to ischemia distally and permanent damage. Examples of this may include strokes and heart attacks. If the blood is sufficiently large, the resulting damage is noticeable and may be able to be treated. However, microscopic blood clots may spread to the entire body. The widespread microscopic clots develop without causing noticeable symptoms of a dangerous situation and may not be detected and treated early until too late.

Echocardiogram abnormalities are seen in convalescent convert patients. Cardiac MRI, echocardiogram, high sensitivity cardiac troponin I, D-dimer, CRP and IL-6 can be used to diagnose and monitor cardiovascular damages and chronic inflammations in convalescent patients of COVID-19 infection. If the finding is positive, anticoagulants such as heparin, warfarin, enoxaparin sodium, acetylsalicylic acid, clopidogrel, apixaban, dabigatran, rivaroxaban, and edoxaban can be used in various dosage tailored to the severity of lingering effects. Treating a coronavirus infected patient with statin or statin plus eicosapentaenoic acid (EPA) at 2 grams twice daily (b.i.d.) can reduce the patient's risks of heart attack, stroke, and cardiovascular damage during the coronavirus infection and prevent subsequent post-acute residual and chronic damage.

Besides treating blood clots, continued endothelial protection is warranted. The endothelium is the lining of all blood vessels, which nourishes all the organs of the body. Diosmiplex 630 mg, one to three times daily, can be used to reduce inflammation, pain, swelling, erythema, neuropathic pain and promote ulcer healing. The amount taken daily depends on the severity of the condition. For example, one time daily for chronic venous disease; two times daily for lymphedema, Raynauld's phenomenon and artial problem; three times a day for acute hemorrhoid. Diosmiplex contains a purified diosmin glycoside to improve circulation. It increases venous and lymphatic flow thus improving capillary and arterial flow to heal digital ulcers due to microscopic blood clots and endothelial damage. It can be used as treatment for COVID-19 purple toes due to microscopic blood clots to superficial blood vessels. Diosmiplex can down regulate the inflammatory molecules associated with venous hypertension. Improvements may include decreasing pain, swelling, erythema and neuropathic pain which can be seen after 2 to 6 weeks.

A majority of COVID-19 patients have mild to moderate symptoms and recover after 4 to 5 weeks. However, approximately 10% could have lingering illness (namely, "Long COVID") even after they no longer test positive (post-viral). Among the top post-viral illnesses is chronic fatigue which includes syndromes and comorbidities such as sleep disorder, pain, depression, anxiety, cognitive impairment, and orthostatic intolerance. Chronic fatigue can be treated with a multi-pronged approach targeting the following underlying abnormalities: (1) in the nervous system with serotonin-norepinephrine reuptake inhibitors (SNRIs) such as duloxetine, venlafaxine, and milnacipran or antiepileptic drugs such as gabapentin, pregabalin, lidocaine, topiramate, and carbamazepine for pain; tricyclics such as nortriptyline and amitriptyline for sleep improvement and pain; (2) in the musculoskeletal system with muscle relaxants such as tizanidine, baclofen, and cyclobenzaprine; (3) systemic corticosteroids such as fludrocortisone for neurally mediated hypotension, and intermittent pulse of prednisone for severe flare-up. In addition, nonsteroidal anti-inflammatory drugs (NSAIDs) and acetaminophen can also be used to moderate the pain. Vitamin D supplement may be used to help the recovery of the immune system. Other common post-viral symptoms include cough, chest tightness, chest pain, shortness of breath (dyspnea), tachycardia, joint pain, body ache, headaches, brain fog, dizziness, concentration problems, trouble sleeping, chills, sweats, and loss of appetite. Diffuse brain damage is seeing in one third of intensive care unit (ICU) patients causing problem with memory and concentration, hallucination, anxiety and restlessness. As a result, dementia may become a long-term issue.

Nicotinamide riboside (NR) can be used to help improve post COVID-19 recovery in cellular energy, fatigue, neurological and cognitive function. NR functions as a precursor to nicotinamide adenine dinucleotide (NAD+), which is a key component of the body's adenosine triphosphate (ATP) energy cascade. The dosage of NR should start with 250 to 300 mg daily increasing as tolerated to 500 to 1000 mg daily.

If there is significant amount of non-subsiding abnormality in inflammation, T-cell immunosuppressants such as mycophenolate, tacrolimus, and sirolimus can be used. It should be noted that post viral infections have been linked to acute onset of arthritis, diabetes, and thyroid disease. Furthermore, Epstein-Barr virus (EBV) if reactivated can trigger symptoms similar to chronic fatigue syndrome or fibromyalgia Kidneys are also common organs involved after the infection due to blood clots. Scar tissue will develop but the damage may be permanent. Kidney function may appear to be normal initially, however years later, aging and subsequent cardiovascular comorbidity may accentuate previous damage from COVID-19 infection.

It should be noted that a biologic treatment such as TNF-inhibitors, IL-6 inhibitors, JAK-inhibitors, inflammasome pathway related inhibitors, antivirals and any other drugs referenced in this disclosure should be avoided if there is any contraindication according to the drug manufactures.

In response to viral and bacterial infection, reactive oxygen species (ROS), are created. As a result, antioxidants levels, such as glutathione, catalase and super oxide dismutase are diminished. (Note: name in side [ ] is a respective trade name of their owners).

Oxidative stress is partially responsible for pulmonary damage, causing organ failure and acute respiratory distress syndrome (ARDS) during influenza virus infection. N-acetylcysteine (NAC) synergizes with Oseltamivir in studies from lethal influenza infections. In combination with antiviral treatment, antioxidants therapy improves host defense mechanisms, prevent organ injuries and improve survival.

N-acetylcysteine (NAC) is a compound that is made from the amino acid L-Cysteine. It is typically used to improve liver health and promote detoxification. NAC has an additional benefit of being mucolytic.

NAC is frequently taken to increase glutathione synthesis in the liver. This important antioxidant plays a number of roles throughout the body by protecting organs from oxidative damage, reducing inflammation and possibly reducing the risk for numerous diseases including cancer. NAC also has mild anti-viral activity. Glutathione prevents apoptosis of infected cells via inhibition of viral induced caspase activation.

In COVID-19 infection, antivirals medications such as Remdesivir, hydroxychloroquine, and lopinavir/ritonavir [Kaletra] have been suggested to treat early disease to prevent acute respiratory distress syndrome (ARDS).

In late disease, anti-inflammatory and cytokine modulating treatments have been used to suppress the robust cytokine response which is causing ARDS. Tocilizumab [Actemra] is an interleukin 6 (IL-6) receptor antibody which an early uncontrolled study from a Chinese trial has shown to rapidly reduction in fever and improvement in oxygenation. Sarilumab [Kevzara] is another IL-6 receptor inhibitor which is being studied for treatment of critically ill COVID-19 patients with multisystem failure.

Disclosed herein is a method to use antioxidants such as N-acetylcysteine (NAC) 1000 milligrams (mg) twice a day, as a preventative pretreatment to boost the immune system. In alternative embodiments, other antioxidants may also be used in case NAC is not available. Once a patient is symptomatic with mild disease of fever and/or mild/moderate cough (e.g., days 1 to 7) there is added hydroxychloroquine 200 mg "bis in die" (b.i.d.) for 10 days. Oseltamivir should also be added if influenza testing is positive.

With the onset of shortness of breath, moderate disease activity, usually around day 7, oral lopinavir/ritonavir [Kaletra] 200 mg/50 mg two tablet twice a day should be added to the antioxidant. There should be avoided a combination of lopinavir/ritonavir [Kaletra] with hydroxychloroquine which may cause serious arrhythmia and drug interactions due to an increased QT interval.

Tocilizumab [Actemra] or Sarilumab [Kevzara] sub Q injections should be considered early (e.g., between days 7 and 15) for patients with moderate to severe elevated C-reactive protein (CRP) and pneumonia, before the onset of ARDS and sepsis. Once a patient is hospitalized, Remdesivir should be considered early, before the need of intubation, onset of sepsis or ARDS.

In summary, NAC should be used for preventative treatment to boost immune system and add antivirals/anti-inflammatory treatment early before the onset of sepsis or ARDS. The method can comprise using an antioxidant, such as N-acetylcysteine (NAC) which is available at low cost without prescription, 1000 mg twice a day, as a preventative pretreatment to boost the immune system. Note that during viral infection, oxidative stress is partially responsible for pulmonary damage, causing organ failure and acute respiratory distress syndrome (ARDS). Once a patient is symptomatic with mild disease of fever and/or mild/moderate cough, (e.g., days 1 to 7), then add hydroxychloroquine 200 mg twice a day for 10 days. Oseltamivir should also be added if influenza testing is positive. With the onset of shortness of breath, moderate disease activity, usually around day 7, oral Lopinavir/Ritonavir [Kaletra] 200 mg/50 mg two tablets twice a day should be added to the antioxidant as an outpatient. Please note to avoid the combination of Lopinavir/Ritonavir with hydroxychloroquine, which may cause serious arrhythmia and drug interactions due to an increased QT interval. For patients with moderate to severe elevated CRP and mild pneumonia (usually between days 7 and 15), IL-6 inhibitors, (e.g, Tocilizumab or Sarilumab) subcutaneous (sub Q) injections may be considered as an outpatient, before the onset of ARDS and sepsis. Since cytokines and chemokines produced as part of host response to the infection contribute to the pathogenesis of tissue damage. Once a patient is hospitalized, considered early use of Remdesivir intravenous (IV), Tocilizumab IV or Sarilumab IV, before the need of intubation, onset of sepsis or ARDS.

Key References: Clinical Characteristics of Coronavirus Disease 2019 in China, *New England Journal of Medicine*, Feb. 28, 2020; Kwak Sung Sun, Physicians Workout Treatment Guidelines for Coronavirus. *Korea Biomedical Review*, Updated Feb. 13, 2020; Katia Aquilano et al, Glutathione: New Role in Redox Signaling for an Old Antioxidant. *Frontiers in the Pharmacology*, 26 Aug. 2014. Comprehensive COVID-19 Treatment Plan Referring to FIG. 2, acute COVID-19 infection can be expressed in three stages based on the symptoms, i.e., mild, moderate, and severe stage for treatment options. The symptoms of the mild stage include sore throat, fever, dry cough, fatigue, diarrhea, lost of taste, smell and others. The symptoms of the moderate stage include dyspnea and hypoxia. The symptoms of the severe stage include acute respiratory distress syndrome (ARDS) and possibly a critical condition known as "cytokine storm". Depending on the individual patient, the COVID-19 infection may have no symptoms, or have only mild symptoms, or progress to the moderate stage, or progress to the severe stage. The dates listed in the timeline may vary and are shown approximately. The following discloses a treatment plan combining immunomodulators and antivirals for COVID-19 based on the status of disease stage, the biomarkers of the patient, and progress of the disease. The strategy of this therapy is to stay one step ahead of the virus invasion thus minimizing the severity and the damages caused by the infection.

PREPARATION (BEFORE EXPOSURE):

1) Diagnose and treat to target co-morbidities, such as diabetes, hypertension, lung diseases, obesity. Reduce cardiovascular risks with statins or statins plus eicosapentaenoic acid (EPA).

2) Boost immune system with N-acetyl cysteine (NAC) 2000 mg daily, vitamin D3 2000 IU daily, prebiotic/probiotic.

3) Wear mask, practice social distancing and contact tracing.

4) Stop cigarette smoking, marijuana smoking, cigar smoking, and vaping.

5) Use Prevnar 13, Pneumovax 23 and influenza vaccination according to CDC guidelines.

AFTER ACUTE EXPOSURE or HIGH RISK EXPOSURE:

1) Continue or begin NAC 2000 mg daily.

2) Plus use hydroxychloroquine 400 mg twice a day on first day as soon as possible, then decreased to 200 mg twice a day for 5 to 10 days.

3) COVID-19 antigen testing.

4) Influenza rapid testing.

5) Blood tests: CRP, CBC with differential, comprehensive metabolic panel, including liver functions, LDH, CPK, D-dimer, G6PD 6) Fever workup, blood and urine culture, chest x-ray, EKG, If elevated D-dimer, obtain CT angiogram to rule out PE, lower extremity ultrasound to rule out DVT.

ANY MILD TO MODERATE COVID-19 SYMPTOMS TREAT AS OUTPATIENT:

1) Hydroxychloroquine 400 mg twice a day on first day ASAP, then decreased to 200 mg twice a day for 5 to 10 days; or 2) Use a TMPRSS2 inhibitor antiviral such as nafamostat or camostat (if available), add a 3CLpro inhibitor antiviral such as lopinavir-ritonavir 200/50 mg 2 tablets twice a day for 5 to 10 days. Do not use lopinavir-ritonavir with hydroxychloroquine which may cause prolonged QT interval and dysrhythmia.

3) Oxygen supplementation to keep oxygen saturation>93%.

4) Prone or lying on the side to improve oxygenation.

5) Treat Co-infections:

a) Treat influenza with oseltamivir.

b) Treat bacterial infection with antibiotic.

6) Avoid using azithromycin with hydroxychloroquine, which may cause prolonged QT interval, dysrhythmia.

IF MODERATE SHORTNESS OF BREATH or O2 SATURATION IN THE LOW 90s, despite oxygen supplementation+prone/side positioning.

1) Add IL-6 inhibition as outpatient, if elevated CRP; avoid if ANC<2000, platelet<150,000, LFTs>1.5x.

2) Tocilizumab 4-8 mg per kilogram IV or 162 mg sub Q, or sarilumab 200 mg.

3) Consider convalescent plasma treatment as outpatient.

4) Consider an RdRp inhibitor such as remdesivir IV treatment, or favipiravir oral (which is more convenient for an outpatient).

5) Consider favipiravir 1.6 g twice daily on day 1, followed by 600 mg twice daily 6) May consider dexamethasone, but be cautioned about increased risk of infection.

7) Consider anticoagulation especially if D-dimer is elevated, with heparin, warfarin, enoxaparin sodium, acetylsalicylic acid, clopidogrel, or direct oral antico-agulants (DOACs) such as apixaban, dabigatran, riva-roxaban, and edoxaban.

8) Use a biologic immunomodulator (TNF-inhibitor-, IL-6 inhibitor, JAK-inhibitor, or inflammasome path-way related inhibitor) if CRP is significantly elevated indicating possible onset of cytokine storm. However, avoid JAK-inhibitor if D-dimer is elevated.

HOSPITALIZATION (Moderate and Sever stage)

1) Add a biologic immunomodulator-(TNF-inhibitor, IL-6 inhibitor, JAK inhibitor, or inflammasome pathway related inhibitor) as outpatient, if elevated CRP; avoid if absolute neutrophil count (ANC)<2000, plate-let<150,000, LFTs>1.5x. Avoid JAK-inhibitor if D-di-mer is elevated.

2) Tocilizumab 4-8 mg per kilogram IV or 162 mg sub Q, or sarilumab-200 mg.

3) Consider convalescent plasma treatment.

4) Consider an RdRp inhibitor such as remdesivir Intra-venous treatment or favipiravir.

5) May consider dexamethasone, but be cautioned about increased risk of infection Consider anticoagulation especially if D-dimer is elevated, with heparin, warfa-rin, enoxaparin sodium, acetylsalicylic acid, clopi-dogrel, or direct oral anticoagulants (DOACs) such as apixaban, dabigatran, rivaroxaban, and edoxaban.

6) May consider a biologic immunomodulator (TNF-inhibitor, IL-6 inhibitor, JAK inhibitor, or inflamma-some pathway related inhibitor) if CRP is significantly elevated indicating possible onset of cytokine storm.

7) Add dexamethasone for acute respiratory distress syn-drome (ARDS).

8) Add ICU/intubation/ECMO/dialysis as needed.

Many of the medicines and methods discussed herein may be used with light enhancement on cells to increase the effectiveness of the medicines. Incorporated herein by ref-erence in its entirety is U.S. patent application Ser. No. 17/071,994 with a filing date of Oct. 15, 2020, entitled "Photon Enhanced Medication System and Methods" which discusses these techniques.

The methods, systems, chemical compounds, small-mol-ecule drugs, biologic immunomodulators and devices dis-cussed above are examples. Various embodiments may omit, substitute, or add various procedures or components as appropriate. For instance, in alternative configurations, the methods described may be performed in an order different from that described, and/or various stages may be added, omitted, and/or combined. Also, features described with respect to certain embodiments may be combined in various other embodiments. Different aspects and elements of the embodiments may be combined in a similar manner. Also, technology evolves and, thus, many of the elements are examples that do not limit the scope of the disclosure to those specific examples.

Specific details are given in the description to provide a thorough understanding of the embodiments. However, embodiments may be practiced without these specific details or limit to the specific mutation or type of coronavirus.

Coronavirus (including SARS-COV2) infection's symp-toms, disease progress, onset days, and severity stages duration may vary depending on individual's viral exposure (inoculum), health status, history and pre-existing condi-tions. This description provides example embodiments only, and is not intended to limit the scope, applicability, or configuration of the disclosure. Rather, the preceding description of the embodiments will provide those skilled in the art with an enabling description for implementing embodiments of the disclosure. Various changes may be made in the function and arrangement of elements without departing from the spirit and scope of the disclosure. There-fore, the foregoing embodiments are presently by way of example only; the scope of the present disclosure is to be limited only by the claims. For example, the methods disclosed herein are not limited to coronavirus nor any strain of COVID-19, but may be used for other viruses as well.

Also, some embodiments were described as processes. Although these processes may describe the operations as a sequential process, many of the operations can be performed in parallel or concurrently. In addition, the order of the operations may be rearranged. A process may have addi-tional steps not included in the figures. Also, a number of steps may be undertaken before, during, or after the above elements are considered.

The invention claimed is:

1. A method for pretreating and treating Covid-19 infec-tion and post-Covid illness in a patient in need thereof comprising:

pretreating the patient with N-acetyl cysteine (NAC) daily before Covid-19 exposure;

treating the patient with a 3C-Like protease (3Clpro) inhibitor for inhibiting viral replication after the Covid-19 infection; and treating the patient with N-acetyl cysteine (NAC) after the Covid-19 infection in the range of 600 to 3000 milli-grams (mg) daily after the Covid-19 infection to improve recovery from organ damage caused by reac-tive oxygen species (ROS) related to inflammation.

2. The method of claim 1, further comprising:

treating the patient with an Interleukin 6 (IL-6) inhibitor for treating hyperinflammation or cytokine storm, if C-Reactive Protein (CRP) or IL-6 is elevated.

3. The method of claim 1, further comprising:

treating the patient with an anticoagulant to prevent stroke or embolic events, if D-dimer is greater than approxi-mately 0.5 micrograms per milliliter.

4. The method of claim 1, further comprising:

treating with a statin and eicosapentaenoic acid (EPA) to reduce the risk of heart attack, stroke, or cardiovascular damage during infection and subsequent post-acute residual damage or chronic damage.

5. The method of claim 1, further comprising:

treating the patient with diosmiplex to improve circulation and to reduce inflammation for endothelial protection.

6. A method for pretreating and treating Covid-19 infec-tion and post-Covid illness in a patient in need thereof comprising:

pretreating the patient with N-acetyl cysteine (NAC) daily before Covid-19 exposure;

treating the patient with an RNA-dependent RNA poly-merase (RdRp) inhibitor for inhibiting viral replication after the Covid-19 infection; and treating with N-acetyl cysteine (NAC) after the Covid-19 infection in the range of 600 to 3000 milligrams (mg)

daily to improve recovery from organ damage caused by reactive oxygen species (ROS) related to inflammation.

7. The method of claim 6, further comprising:

treating the patient with an Interleukin 6 (IL-6) inhibitor for treating hyperinflammation or cytokine storm, if C-Reactive Protein (CRP) or IL-6 is elevated.

8. The method of claim 6, further comprising:

treating the patient with an anticoagulant to prevent stroke or embolic events, if D-dimer is greater than approximately 0.5 micrograms per milliliter.

9. The method of claim 6, further comprising:

treating with a statin and eicosapentaenoic acid (EPA) to reduce the risk of heart attack, stroke, or cardiovascular damage during infection and subsequent post-acute residual damage or chronic damage.

10. The method of claim 6, further comprising:

treating the patient with diosmiplex to improve circulation and to reduce inflammation for endothelial protection.

11. A method for treating Covid-19 infection and post-Covid illness in a patient in need thereof comprising:

pretreating the patient with N-acetyl cysteine (NAC) daily before Covid-19 exposure;

treating the patient with a transmembrane protease serine 2 (TMPRSS2) enzyme inhibitor for inhibiting viral entry to cells after the Covid-19 infection; and treating the patient with N-acetyl cysteine (NAC) after the Covid-19 infection in the range of 600 to 3000 milligrams (mg) daily after the Covid-19 infection to improve recovery from organ damage caused by reactive oxygen species (ROS) related to inflammation.

12. The method of claim 11, further comprising:

treating the patient with an Interleukin 6 (IL-6) inhibitor for treating hyperinflammation or cytokine storm, if C-Reactive Protein (CRP) or IL-6 is elevated.

13. The method of claim 11, further comprising:

treating the patient with an anticoagulant to prevent stroke or embolic events, if D-dimer is greater than approximately 0.5 micrograms per milliliter.

14. The method of claim 11, further comprising:

treating with a statin and eicosapentaenoic acid (EPA) to reduce the risk of heart attack, stroke, or cardiovascular damage during infection and subsequent post-acute residual damage or chronic damage.

15. The method of claim 11, further comprising:

treating the patient with diosmiplex to improve circulation and to reduce inflammation for endothelial protection.

\* \* \* \* \*